US012616443B2

(12) United States Patent
Van Heesch et al.

(10) Patent No.: US 12,616,443 B2
(45) Date of Patent: May 5, 2026

(54) PATCH SENSOR FOR A MEDICAL DEVICE

(71) Applicant: KONINKLIJKE PHILIPS N.V.,
Eindhoven (NL)

(72) Inventors: Franciscus Hendrikus Van Heesch,
Valkenswaard (NL); **McKee Dunn
Poland,** Andover, MA (US)

(73) Assignee: KONINKLIJKE PHILIPS N.V.,
Eindhoven (NL)

( * ) Notice: Subject to any disclaimer, the term of this
patent is extended or adjusted under 35
U.S.C. 154(b) by 727 days.

(21) Appl. No.: 17/442,244

(22) PCT Filed: Mar. 20, 2020

(86) PCT No.: PCT/EP2020/057802
§ 371 (c)(1),
(2) Date: Sep. 23, 2021

(87) PCT Pub. No.: WO2020/193414
PCT Pub. Date: Oct. 1, 2020

(65) Prior Publication Data
US 2022/0142610 A1 May 12, 2022

Related U.S. Application Data

(60) Provisional application No. 62/823,226, filed on Mar.
25, 2019.

(30) Foreign Application Priority Data

Apr. 17, 2019 (EP) ..................................... 19169728

(51) Int. Cl.
*A61B 8/00* (2006.01)
*G10K 11/20* (2006.01)
(Continued)

(52) U.S. Cl.
CPC .......... *A61B 8/4236* (2013.01); *A61B 8/4472*
(2013.01); *A61B 8/4483* (2013.01);
(Continued)

(58) Field of Classification Search
CPC ... A61B 8/4236; A61B 8/4472; A61B 8/4483;
A61B 8/56; A61B 8/0866; G10K 11/20;
H04L 67/12
See application file for complete search history.

(56) References Cited

U.S. PATENT DOCUMENTS 5,823,962 A 10/1998 Lerch
11,075,997 B2 * 7/2021 Rácz ....................... H04L 69/14
(Continued)

FOREIGN PATENT DOCUMENTS

CN 108992091 A1 12/2018
JP 2001127691 A 5/2001
(Continued)

OTHER PUBLICATIONS

International Search Report and Written Opinion, International
Application No. PCT/EP2020/057802, Mailed on May 8, 2020.

*Primary Examiner* — Keith M Raymond
*Assistant Examiner* — Adam D. Kolkin

(57) ABSTRACT

A patch sensor adapted to process echo information to
generate a first type of medical data and/or a second,
different type of medical data using a respective processing
pathway. A communications module of the patch sensor is
adapted to be switchable between a first mode, in which only
the first type of medical data is transmitted to a medical
device, and a second mode, in which at least the second type
of medical data is transmitted to the 5 medical device. The
first type of medical data occupies a smaller bandwidth
(during transmittal) than the second type of medical data.

20 Claims, 2 Drawing Sheets

(51) Int. Cl.
    *A61B 8/08*             (2006.01)
    *H04L 67/12*          (2022.01)

(52) U.S. Cl.
    CPC ................ *A61B 8/56* (2013.01); *G10K 11/20*
            (2013.01); *A61B 8/0866* (2013.01); *H04L*
                                      *67/12* (2013.01)

(56)               References Cited

U.S. PATENT DOCUMENTS

| | | | |
|---|---|---|---|
| 2006/0079782 A1* | 4/2006 | Beach ................. | G01S 7/52026 |
| | | | 600/450 |
| 2007/0161904 A1* | 7/2007 | Urbano ................ | A61B 8/4438 |
| | | | 600/459 |
| 2008/0228045 A1* | 9/2008 | Gao ....................... | G16H 40/67 |
| | | | 600/301 |
| 2010/0284521 A1* | 11/2010 | McBroom ............ | A61B 6/4283 |
| | | | 378/204 |

| | | | |
|---|---|---|---|
| 2012/0065479 A1 | 3/2012 | Lahiji | |
| 2012/0253847 A1* | 10/2012 | Dell'Anno ............ | G16H 40/67 |
| | | | 705/2 |
| 2014/0128735 A1* | 5/2014 | Newell .................... | A61B 8/56 |
| | | | 600/443 |
| 2015/0065882 A1* | 3/2015 | Cho ..................... | A61B 8/4411 |
| | | | 600/443 |
| 2015/0164322 A1 | 6/2015 | Derchak | |
| 2015/0289814 A1 | 10/2015 | Magar | |
| 2017/0007853 A1* | 1/2017 | Alford ..................... | A61B 8/02 |
| 2017/0179774 A1 | 6/2017 | Jin | |
| 2019/0104992 A1 | 4/2019 | Magar | |

FOREIGN PATENT DOCUMENTS

| | | |
|---|---|---|
| JP | 2006051105 A | 2/2006 |
| WO | 2006042201 A1 | 4/2006 |
| WO | 2017011298 A1 | 1/2017 |

* cited by examiner

PATCH SENSOR FOR A MEDICAL DEVICE

This application is the U.S. National Phase application under 35 U.S.C. § 371 of International Application No. PCT/EP2020/057802, filed on 20 Mar. 2020, which claims the benefit of U.S. Provisional Application No. 62/823,226, filed 25 Mar. 2019. These applications are hereby incorporated by reference herein.

FIELD OF THE INVENTION

The present invention relates to the field of medical devices, and in particular to patch sensors for medical devices.

BACKGROUND OF THE INVENTION

Ultrasound imaging has been widely adopted as an imaging technique in the medical field, not least due to its relative ease of use, diagnostic usefulness and good safety record. One recent trend in the ultrasound imaging field is the miniaturization of ultrasound devices, and in particular to the development of wireless handheld device and patch sensors.

In particular, patch sensors are useful for long-term monitoring, as they can be placed on a subject (to be monitored) and left in place for a long period of time, e.g. more than an hour. As patch sensors can be left on a subject for such a long period of time, there has been an increasing interest is appropriating or adapting the patch sensors to enable the monitoring of other parameters of the subject, such as physiological data including vital signs.

Thus, a "hybrid" patch sensor for an ultrasound imaging system can act to both monitor physiological data and obtain ultrasound imaging data, e.g. raw data for constructing an ultrasound image.

There is an ongoing desire to improve the adaptability and flexibility of use for a patch sensor suitable for an ultrasound system.

SUMMARY OF THE INVENTION

The invention is defined by the claims.

According to examples in accordance with an aspect of the invention, there is provided a patch sensor to transmit one or more signals to a medical device. The patch sensor comprises: a transducer array adapted to transmit ultrasound waves and receive echo information to thereby generate a received echo signal; a processing system defining: a first processing pathway adapted to process the received echo signal to generate a first signal carrying a first type of medical data derived from the received echo signal; and a second processing pathway adapted to process the received echo signal to generate a second signal carrying a second, different type of data derived from the received echo signal, the second signal occupying a greater bandwidth than the first signal. The patch sensor also comprises a communications module adapted to transmit one or more signals to the medical device, the communications module being operable in: a first communication mode, in which the communications module transmits only the first signal to the medical device; and a second communication mode, in which the communications module transmits at least the second signal to the medical device.

Thus, a patch sensor (suitable for an ultrasound imaging system) is operable in two modes, a first communication mode in which only a first type of medical data (i.e. "first data") is passed to a medical device and a second communication mode in which a second type of data (i.e. "second data"), being larger than the first data, is passed to the medical device. Thus, a different set of data is sent to the medical device depending upon the communication mode of the patch sensor.

It will be apparent that the two types of medical data are different in size. In particular, the two types of data may be different in size before any formatting or modification is made to the data for transmission or communication, e.g. before any communication metadata is added, before any encoding for communication takes place or the like.

Thus, in the context of the present disclosure, the term "medical data" is used to refer to the data that is transmitted to the medical device and directly correlates to data obtained from the subject for medical purposes, e.g. excluding data sent as part of an encryption, modulation or other communication-based scheme. In other words, the medical data refers to information directly related to monitored parameters of the subject, rather than any communication-based additional data (e.g. compressions, metadata, paddings, encryption, formatting and so on).

In particular, the patch sensor is operable in (at least) two different communication modes, in which communications sent by the patch sensor occupy at least two different bandwidth sizes. Generally speaking, the second signal carries more data or more complex data per second than the first signal. Thus, the bandwidth required to transport the second signal is greater than the bandwidth required to transport the first signal.

The invention relies upon the understanding that differing amounts of medical data would occupy different amounts of bandwidth when transmitted, and proposes to control the amount of bandwidth used by controlling the amount of medical data communicated by the patch sensor.

The greater the bandwidth used to communicate, the larger the power consumption and processing complexity required.

Thus, the patch sensor may be adapted to adjust the amount of resources (e.g. bandwidth or power consumption) that it uses to transmit data to the medical device. In particular, a patch sensor may be adapted to adjust the bandwidth that it uses, for example, to reduce a power consumption of the patch sensor or to acquiesce to a bandwidth available to the patch sensor from the medical device.

An available bandwidth for a patch sensor may vary, for example, based on the communication channels, protocols or methodologies available to the patch sensor. By way of example only, a wired connection to the medical device would have a higher bandwidth availability (e.g. >1 Mbit/s) than a wireless connection (e.g. <100 kbit/s) to a medical device. Similarly, some wireless connections may have a higher bandwidth availability than others (e.g. due to congestion or because of protocol limitations, e.g. 5 GHz vs. 2.4 GHz WiFi, or WiFi vs. Bluetooth link availability).

The proposed concept for using two different communication modes enables selection and control over the bandwidth (as well as other resources, such as power consumption or processing complexity) used by the patch sensor. This selection may be performed automatically, e.g. as later described, or manually, e.g. in response to a user input.

In particular, a same patch sensor can be used to select between two different types of data to send to the medical device. This means that the patch sensor need not be moved from a position (on a monitored subject) for a patient medical device to obtain two different types of data, e.g. for two different types of medical device such as a physiological data monitor or an ultrasound image system (for constructing and/or displaying ultrasound images).

The first signal may, for example, be low-bandwidth information which does not need to be transmitted in real or near-real time, e.g. low-bandwidth ultrasound data or physiological data, such as vital sign measurements.

The second signal may, for example, be high-bandwidth information which would preferably be transmitted in real or near-real time to the medical device, such as raw data for enabling a (near-)real time ultrasound image to be constructed by the medical device for display.

The first signal may have a bandwidth<100 kbits/s (i.e. "low-bandwidth") whereas the second signal may have a bandwidth>1 Mbit/s (i.e. "high-bandwidth"). In particular, in some embodiments, the first signal may have a bandwidth less than the lower bound of the second signal, e.g. no greater than 10 times less than the lower bound of the second signal. These are only example values, and the skilled person would be readily capable of expanding to other bandwidth restrictions for "low" and "high" (i.e. the first and second signals respectively).

In some embodiments, a processing pathway of the processing system may be deactivated based on the communication mode. For example, the second processing pathway may be deactivated if the communications module is in the first communication mode. In other examples, the first processing pathway may be deactivated if the communications module is in the second communication mode. Such embodiments reduce a power consumption by the patch sensor.

In yet other embodiments, an activation or deactivation of the processing pathways may define which communication mode the communications module is in. For example, if the second processing pathway is deactivated (e.g. by a user), the communications module may be switched into the first communication mode (and vice versa).

Thus, if the communications module is in the first communication mode, the second processing pathway may be deactivated and if the communications module is in the second communication mode, the first processing pathway may be deactivated.

Here, the term "deactivated" means bypassed, unused or otherwise rendered non-functional (i.e. so that the first/second signal is not generated or output by the processing system, depending upon which pathway is deactivated). A deactivated pathway will preferably be configured to consume little, negligible or no power.

Preferably, the first type of medical data (i.e. the "first data") is physiological data and the second type of medical data (i.e. the "second data") is ultrasound imaging data. Physiological data, such as identified vital sign information, a measured heartrate, blood pressure (i.e. systolic and/or dystolic pressure), vascular vessel size and/or distensibility and so on, can be obtained using ultrasound imaging techniques, as would be well known to the skilled person. Ultrasound imaging data may, for example, comprise a conventional (2D or 3D) representation of an ultrasound image, e.g. raw data for enabling an ultrasound image/video to be (re)constructed for display to a user.

Accordingly, the communication module may be adapted to: when operating in the first communication mode, transmit the first signal to a physiological data monitor which thereby acts as the medical device; and when operating in the second communication mode, transmit at least the second signal to an ultrasound monitoring system which thereby acts as the medical device.

The communications module may comprise a wireless transmitter, and the communications module may be adapted to, when operating in the first communication mode, wirelessly transmit the first signal to the medical device using the wireless transmitter.

Thus, the first communication mode may be operational when a wireless transmitter is available. In particular, the first communication mode may comprise sending the first signal to the medical device via a wireless communication channel.

Typically, wireless communications have a relatively low bandwidth, and it would therefore be preferred to send only a relatively low bandwidth signal (here, the first signal) when using a wireless communication. Similarly, as low bandwidth signals need not use a higher bandwidth communication channel (such as a wire), it is possible to use lower bandwidth communication channels, such as a wireless channel, which may be preferred, e.g. for subject comfort.

Furthermore, when operating wirelessly, a patch sensor may be power resource restricted, e.g. be powered by a battery or solar cell. Thus, it would be preferred to reduce a power consumption of the patch sensor. The present invention may operate in the first communication mode when communicating wirelessly to minimize the power consumption of the patch sensor, i.e. by communicating using a lower bandwidth signal.

In some embodiments, the communications module comprises a wired terminal, for connecting to a wire connected to the medical device, and the communications module may be adapted to, when operating in the second communication mode and if a wire is connected to the wired terminal, transmit at least the second signal to the medical device over the wire connected to the wired terminal.

Thus, the second communication mode may be operational when a wired connection to the medical device is available. A wire can carry or facilitate the transport of a relatively high bandwidth signal (e.g. due at least to reduced noise or absence/reduced number of other signals carried by the wire). Thus, if a wired connection to the medical device is available, it would be preferred to send a relatively higher bandwidth signal, to maximize the information transmitted to the medical device.

Furthermore, when connected to the medical device over a wire, a patch sensor may not be resource-restricted, e.g. may be powered by a mains supply, e.g. using the wire. Thus, there may be no restriction on the power consumed by the patch sensor. The patch sensor may therefore operate in the second communication mode when communicating over a wire to maximize the information transmitted to the medical device (as there is no restriction on the power that the patch sensor can use).

The patch sensor may further comprise a communication mode controller adapted to control a communication mode of the communications module. The communication mode is controlled based on information about one or more resources available to the patch sensor.

The information about one or more resources may comprise information about: a type of power source used by the patch sensor; a type of medical device a power level of a power source used by the patch sensor; and an available bandwidth for communicating with the medical device.

Thus, the selected communication mode may depend upon a type of power source available to the patch sensor, a power level (e.g. remaining battery level) of the power source and/or an available bandwidth for communicating with the medical device. Other suitable resource levels will be apparent to the skilled person.

Preferably, the communication mode controller is adapted to determine and use information about an available bandwidth, for communicating with the medical device, to select a communication mode for the communications module. Thus, an automatic determination as to which of the first and second communication modes should be used can be made based on an available bandwidth for communicating with the medical device.

In particular, the communication mode controller may place the communications module in the first communication mode if there is insufficient bandwidth to transmit the second signal to the medical device. Similarly, the communication mode controller may place the communications module in the first communication mode if there is sufficient bandwidth to transmit at least the second signal to the medical device.

In one example, the communication mode controller is adapted to: identify one or more available communication channels over which the communications module is able to communicate with the medical device; determine whether or not any of the identified communication channels have sufficient bandwidth to facilitate the transport of the second signal to the medical device; and place the communications module in the second communication mode in response to determining that at least one of the identified communications channels has sufficient bandwidth to transmit the second signal to the medical device.

Thus, if a channel (between the patch sensor and the medical device) has sufficient bandwidth to transmit/carry (i.e. facilitate the transport of) at least the second signal, then the patch sensor may be placed in the second communication mode (so as to transmit the second signal to the medical device). Of course, the channel used to transmit the second signal to the medical device may comprise the channel identified by the communication mode controller as having sufficient bandwidth to facilitate the transport of (or otherwise carry) the second signal.

Here, the term "sufficient bandwidth" refers to a state in which an available or existing communication channel from the patch sensor to the medical device is able to carry the second signal with a minimum reliability, e.g. if there is at least one unoccupied (by other signals) channel having sufficient bandwidth to transmit the second signal.

This has the result of ensuring that the second signal (having a larger bandwidth and thereby carrying more information) is transmitted to the medical device when there is sufficient bandwidth for it to be carried to the medical device.

The communication mode controller may be adapted to place the communications module in the first communication mode in response to determining that none of the identified communications channels has sufficient bandwidth to transmit the second signal to the medical device. The patch sensor may therefore default to the first communication mode, so that at least some information is transmitted to the medical device, if there is not sufficient bandwidth to communicate the second signal to the medical device.

In some embodiments, the communications module comprises a wired terminal, for transmitting one or more signals via a wire connected thereto; and the communication mode controller is adapted to: determine whether a wire is connected between the wired terminal and the medical device to thereby identify whether a wired communication channel to the medical device is available; and place the communications module in the second communication mode in response to determining that the wired communication channel is available.

It is recognized that a wired connection between the patch sensor and medical device will provide sufficient bandwidth to facilitate the transport of the second signal to the medical device. Thus, the steps of identifying available communication channels and determining whether any have sufficient bandwidth can be combined into a single step of identifying whether a wired connection is available.

Determining whether a wire is connected between the wired terminal and the medical device may be performed, for example, by using known any method of detecting whether a wire is connected to a wired terminal (e.g. by monitoring impedance at the wired terminal or even using proximity sensors).

The communications module may be adapted to, when operating in the second communication mode and if a wire is connected to the wired terminal, transmit at least the second signal to the medical device over a wire connected to the wired terminal in response to determining that the wired communication channel is available.

Preferably, the wired terminal is a universal serial bus (USB) terminal, so that a wired connection formed between the communications module and the medical device is a USB connection. A USB connection enables communications at around 50 Mbits/s. Thus, in some embodiments, the second signal may use a bandwidth of up to 50 Mbits/s, e.g. no more than 50 Mbits/s. Thus, in some embodiments, the second signal may have a bandwidth of from 1 Mbits/s to 50 Mbits/s, e.g. from 5 Mbits/s to 50 Mbits/s. It will be clear that the first signal should have a bandwidth less than the lower bound of the second signal, e.g. no greater than 10 times less than the lower bound of the second signal.

A USB connection between the communications module and the medical device further enables the patch sensor to be powered by the medical device.

Other wired connections between the communications module and the medical device are possible, a USB connection being only one example. Other wired connections could include, for example, interfaces according to the IEEE 1394 standard (FireWire), Thunderbolt, I2C technologies and so on. The wired terminal may be adapted accordingly. These other wired connections may also enable the medical device to power the communications module.

In some embodiments, the communications module comprises a wireless transmitter for transmitting signals to the medical device; and the communication mode controller is adapted to: identify one or more available wireless communication channels over which the wireless transmitter is able to transmit a signal to the medical device; determine an available bandwidth of each available wireless communication channel; determine whether or not any of the identified available wireless communication channels have sufficient available bandwidth to facilitate the transport of the second signal to the medical device; and place the communications module in the second communication mode in response to determining that the at least one wireless communication channel has sufficient bandwidth to facilitate the transport of the second signal to the medical device.

Preferably, such a communications module is adapted to, when operating in the second communication mode, wirelessly transmit at least the second signal to the medical device using the wireless transmitter if a wired communication channel is not available.

In preferred embodiments, if a wired communication channel is available, the second signal will be transmitted using the wired communication channel. This improves a reliability of the transmitted of the second signal to the medical device.

However, in some other embodiments, the second signal may be transmitted by a wireless communications channel if the wireless communication channel has sufficient bandwidth to transport the second signal. Using a wireless transmission channel may improve the comfort to the monitored subject, e.g. as uncomfortable wires need not be used.

Other methods of selecting the communication mode for the communications module are envisaged.

For example, the communication mode controller may determine a type of power source used by the patch sensor. In response to the power source being a resource-restricted type (e.g. a battery or a solar cell), the communication mode controller may place the communications module in the first communication mode. In response to the power source not being a resource-restricted type (e.g. powered by a mains supply), the communication mode controller may place the communications module in the second communication mode.

In another example, the communication mode controller may determine a (remaining) power level of a power source used by the patch sensor.

For instance, if a power source used by a patch sensor is a battery, the communication mode controller may place the communications module in the first communication mode in response to a remaining power level falling below a predetermined value (e.g. below 50% or below 25%). The predetermined power level may be any value in the region of from 10% to 60% of the maximum available power level, for example, from 10% to 40%, for example, from 15% to 30%, for example, 20%.

Of course, a combination of factors could be used to define whether the first or second communication modes are used. In one example, the communication mode controller may place the communications module in the second communication mode only if the power source is not a resource-restricted type and there is sufficient bandwidth to transmit the second signal to the medical device. Otherwise, the communication mode controller may place the communications module in the first communication mode.

In some embodiments, the communications module is adapted to, when operating in the second communication mode, transmit both the first signal and the second signal to the medical device.

Of course, in such embodiments, the first processing pathway cannot be deactivated when in the second communication mode. However, in some embodiments, the second processing pathway may still be deactivated when the communications module is in the first communication mode.

Moreover, the communications module may be operable in a third communication mode, in which only the second signal is transmitted to the medical device. A communication mode controller may place the communications module in the third communication mode based on information about available resources of the patch sensor. For example, the communication mode controller may place the communications module in the third communication mode if there is sufficient bandwidth to transmit the second signal, but insufficient bandwidth to transmit both the first and second signal, to the medical device.

In some embodiments, the communications module may be operable in a non-communicative mode, in which no signals are transmitted to the medical device. The communications module may enter the non-communicative mode, for example, if there is insufficient bandwidth to transmit the first signal.

The patch sensor may further comprise a subject securing mechanism adapted to secure the patch sensor to a position on the subject, wherein the communications module is adapted to be switchable between (at least) the first and second communication mode whilst the patch sensors remains in the same position on the subject.

An underlying advantage of the present invention is that a patch sensor is able to send two different types of information without needing to change position on the subject by simply switching its communication mode. This switching may, as previously described, be performed automatically, e.g. in response to a wire being connected to the sensor or if a wireless communication channel having sufficient bandwidth becomes available.

This advantage is realized, in particular, if a subject securing mechanism is able to secure the patch sensor to the subject, so that a position of the patch sensor is fixed on the subject. The subject securing mechanism may comprise, by way of example only, (soft) adhesive, one or more straps or bands (e.g. comprising a hook-and-loop fastening mechanism), a skin implanting mechanism and so on.

In some examples, the communication mode of the communications module may be defined by a user input or user override. Thus, a user may be able to select whether a first or second signal is transmitted to the medical device by the communications module. The patch sensor may therefore comprise a user interface (not shown) to enable a user to control the communication mode of the communications module. This user interface may be adapted to override any automated mode selection of the communication mode controller (if present).

In some other examples, the communication mode of the communications module may be based upon the type of medical device with which the communications module is communicating. The communications module may therefore receive an indication of the type of the medical device, and set a communications mode based on this indication. This indication may be transmitted by the medical device (and received at the communications module) or received from a user input.

For example, if the first signal carries physiological data and the second signal carries ultrasound imaging data, the communications module may operate in the first communication mode if the medical device is a physiological monitor and operate in the second communication mode if the medical device is an ultrasound imaging device.

According to examples in accordance with an aspect of the invention, there is also provided a monitoring system comprising: one or more patch sensors previously described; and a medical device adapted to receive at least one signal from each patch sensor.

The medical device may, for example, comprise an ultrasound imaging monitor adapted to display an ultrasound image (e.g. if the second signal carries ultrasound imaging data). The medical device may be adapted to, for example, receive raw ultrasound data from at least one patch sensor to construct or reconstruct an (2D or 3D) ultrasound image from the raw ultrasound data. Methods of constructing or reconstructing an ultrasound image from raw ultrasound data will be readily apparent to the skilled person.

In another example, the medical device may comprise a physiological data monitor adapted to monitor and store physioloigcal parameters of the patient.

According to examples in accordance with an aspect of the invention, there is also provided a method of controlling a communication mode of any described patch sensor. The method comprises identifying one or more available communication channels over which the communications module is able to communicate with the medical device; determining whether or not any of the identified communication channels have sufficient bandwidth to facilitate the transport of the second signal to the medical device; placing the communications module in the second communication mode in response to determining that at least one of the identified communications channels has sufficient bandwidth to transmit the second signal to the medical device; and placing the communications module in the first communication mode in response to determining that none of the identified communications channels has sufficient bandwidth to transmit the second signal to the medical device.

According to examples in accordance with an aspect of the invention, there is also provided computer program comprising code means for implementing any described method when said program is run on a processing system.

These and other aspects of the invention will be apparent from and elucidated with reference to the embodiment(s) described hereinafter.

US 2019/104992 A1 (MAGAR SURENDAR [US] ET AL) 11 Apr. 2019 discloses a wireless physiological patch sensor. In an embodiment, the patch sensor can transmit using either ultrawide band radio and narrowband radio.

US 2017/0179774 A1 (JIN GIL-JU [KR] ET AL) 22 Jun. 2017 discloses a wireless uptrasound probe and a method of charging a battery in the wireless ultrasound probe.

US 2015/164322 A1 (DERCHAK P ALEXANDER [US]) 18 Jun. 2015 discloses a multi-modal method and system for transmitting information about a subject. The system including a data acquisition subsystem configured to generate a first signal and a second signal, each representing a physiological characteristic of the subject.

CN 108 992 091 (SUZHOU BEILAIFU MEDICAL TECH CO LTD) 14 Dec. 2018 discloses a fetal monitoring telemetering device. The device can switch between a wired and wireless communication mode during fetal monitoring.

US 2014/128735 A1 (NEWELL TODD [US] ET AL) 8 May 2014 discloses a system that utilizes separate data signal to transmition both high-resolution data and low-latency synchronization data utilizing different wireless protocols.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
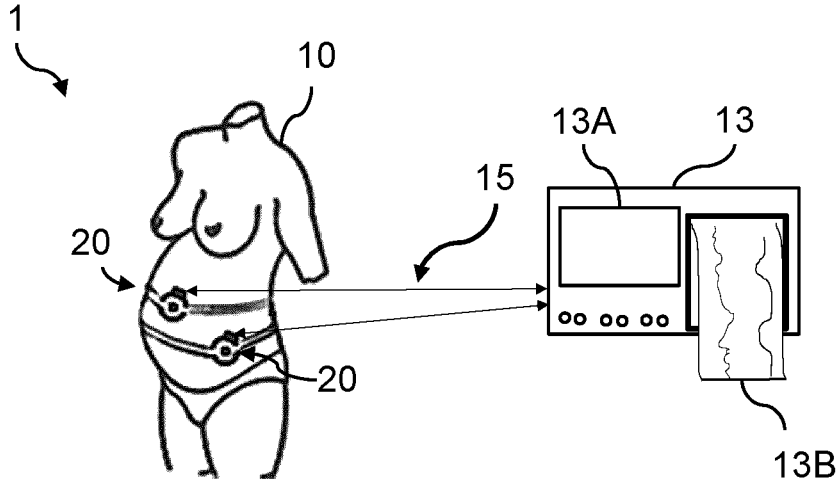
FIG. 1 illustrates a monitoring system for understanding a context of the present invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

According to a concept of the invention, there is proposed a patch sensor adapted to process echo information to generate a first type of medical data ("first data") and/or a second, different type of medical data ("second data") using a respective processing pathway. A communications module of the patch sensor is adapted to be switchable between a first mode, in which only the first data is transmitted to a medical device, and a second mode, in which at least the second data is transmitted to the medical device. The first data occupies a smaller bandwidth (during transmittal) than the second data.

Embodiments are at least partly based on the realization that a patch sensor with ultrasound capabilities can be adapted to generate at least two different types of signal, having different bandwidths, which can be exploited to adapt to different bandwidth, power or processing complexity requirements or to be used in different patient monitoring or diagnosis systems.

Illustrative embodiments may, for example, be employed in patient monitoring systems in a clinical setting, such as a hospital. In particular, a described patch sensor may be used for different monitoring systems, such as an ultrasound imaging system and a physiological monitoring system, without needing to be (re)moved with respect to a monitored subject.

A "patch sensor" is a wearable and flexible sensor that is typically capable of molding to the contours of a subject to which it is attached.

Patch sensors suitable for an ultrasound imaging system, e.g. by generating raw data suitable for constructing an ultrasound image/video, would be well known to the person skilled in the art. It should be noted that just because a patch sensor is suitable for use with an ultrasound imaging system, this does not prevent the patch sensor from also being suitable for use with other patient monitoring systems, such as physiological data monitors (e.g. a heartrate monitoring system or a blood pressure monitoring system).

FIG. 1 illustrates a monitoring system 1, such as an ultrasound imaging system, for understanding a context of the invention.

The monitoring system comprises one or more patch sensors 20, embodiments of which will be later described. A patch sensor 20 is disposed on a subject 10 and monitors or obtains data about that subject, e.g. using ultrasound transmissions. A patch sensor 20 may be connectable to the subject using an appropriate adhesive, such as a weak or gummy adhesive. Other methods of connecting a patch sensor, e.g. using one or more elastic or hook-and-loop belts (as illustrated) would be known.

Each patch sensor 20 is adapted to communicate with a medical device 13 of the monitoring system 1. In particular, each patch sensor is adapted to transmit at least one signal to the medical device. Each patch sensor is adapted to be able to communicate at least wirelessly with the monitoring system, and is preferably further adapted to be able to communicate with the monitoring system over a wire (e.g. which may be plugged or unplugged to the patch sensor). The medical device 13 receives communications from each patch sensor 20.

Each patch sensor 20 is suited for use with an ultrasound imaging system. Thus, each patch sensor may be adapted to obtain and transmit ultrasound information to the medical device, suitable for enabling a medical device to construct or reconstruct an ultrasound image.

The communication path 15 between the one or more patch sensors 20 and the medical device 13 can be wired and/or wireless. Each patch sensor is adapted to be operable so as to communicate at least wirelessly with the medical device.

Suitable wireless communication protocols that may be used include an infrared link, ZigBee®, Bluetooth®, a wireless local area network protocol such as in accordance with the IEEE 802.11 standards, a 2G, 3G or 4G telecommunication protocol, and so on. Other formats will be readily apparent to the person skilled in the art.

In an embodiment, a patch sensor is waterproof to thereby be usable under water, for example, in a bathtub or under the shower. The patch sensor may therefore be configured to use frequencies for which the attenuation of radio transmission in water is relatively low. In particular, the patch sensor may be configured to not use the 2.4 GHz ISM band which is used by ZigBee®, Bluetooth®, IEEE 802.11, and so on. Instead, the patch sensor may be configured to use a sub GHz range frequency band. In an embodiment, the patch sensor is configured to use the ISM band at 433 MHz in Europe and some other regions or the WMTS band at 608 MHz in the US or the T108 band at 920 MHz in Japan.

Suitable wired communication protocols that may be used include universal serial bus (USB), the IEEE 1394 standard (FireWire), Thunderbolt, I2C and so on. Other formats will be readily apparent to the person skilled in the art.

The medical device 13 may comprise, for example, a display 13A (e.g. for displaying an ultrasound image) and/or a printer 13B, e.g. for printing measurements obtained by the patch sensors for long-term monitoring. Preferably, the medical device 13 is able to construct or reconstruct an ultrasound image/video from raw ultrasound data for display on the display 13A, e.g. using a medical device processing system (not shown).

In particular, the medical device 13 is adapted to receive signals from each sensor and process said signals, e.g. to identify a physiological parameter such as heart rate or to construct an ultrasound image. The output of the processing may be provided on a display or printed.

Each patch sensor may be battery operated and/or able to be powered from a mains supply. By way of example only, if the patch sensor is connected via one or more wires to a medical device, the medical device may power the patch sensor over a wire.

It should be noted that, although FIG. 1 shows two patch sensors 20, the medical device 13 could also communicate with more than two patch sensors 20 or with only a single patch sensor 20.

Figure 2:
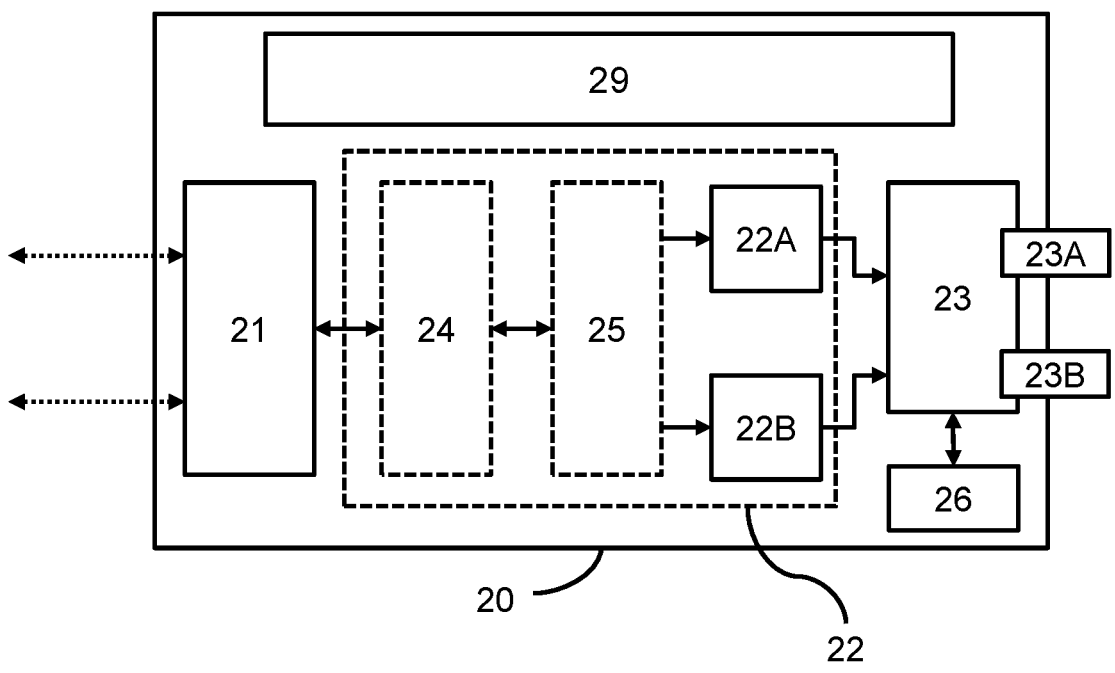
FIG. 2 is a block diagram illustrating a patch sensor according to an embodiment.

FIG. 2 is a block diagram illustrating a patch sensor 20 according to an embodiment of the invention.

The patch sensor 20 comprises a transducer array 21 adapted to transmit ultrasound waves and receive echo information to thereby generate a received echo signal. The transducer array 21 may, for example, one or more individual transducer elements, e.g. 2 transducer elements, 4 transducer elements and/or 8 transducer elements.

The patch sensor 20 further comprises a processing system 22 adapted to process the received echo signal from the transducer array.

The processing system 22 defines a first processing pathway, e.g. comprising at least a first processing element 22A, that generates a first signal carrying a first type of medical data ("first data"). The processing system 22 further defines a second processing pathway, e.g. comprising at least a second processing element 22B, that generates a second signal carrying a second type of medical data ("second data"). It will be apparent that the first processing pathway does not comprise the second processing element 22B and the second processing pathway does not comprise the first processing element 22A. Thus, the first and second processing pathway may comprise one or more elements unique to that pathway (or at least, not shared with the other of the first and second processing pathway).

In some embodiments, the second processing pathway comprises the entirety of the first processing pathway, with at least one additional unique element or vice versa. Thus, at least one of the first and second processing pathways may comprise a processing element not found in the other of the first and second processing pathways.

The first and second data, and therefore the first and second signal, are different from one another. In particular, a bandwidth of the second signal is greater than the bandwidth of the first signal. Put another way, the second signal attempts to transmit more data per second (e.g. in Kbps) than the first signal. Thus, the size of the first data (over a set period of time) may be smaller than the size of the second data (over that same period).

The bandwidth required to transmit the first and/or second signal can be easily calculated.

The patch sensor 20 further comprises a communications module 23 operable in a first and second, different communication mode. The communications module is adapted to transmit or communicate one or more signals to a medical device, such as an ultrasound monitoring system or physiological data monitor.

The communications module 23 is adapted to communicate using wireless and, optionally, wired communication channels or means. Thus, the communications module may comprise a wireless transmitter or transceiver 23A, for communicating wirelessly with the medical device, and optionally a wired terminal 23B, for receiving a wire or cable connected to the medical device.

The wired terminal 23B, if present, may be adapted to selectively receive a wire (for connecting to the medical device), thereby being engage-able with a wire connected to the medical device. Thus, a wire may be plugged and unplugged to/from the wired terminal 23B.

Preferably, the wired terminal 23B is arranged on the patch sensor so as to be exposed to a user when the patch sensor is secured to the subject (e.g. by an adhesive). This means that a wire or cable to the medical device can be connected to the patch sensor without needing to rearrange or move a position of the patch sensor on the subject.

The wireless transceiver may be adapted to communicate using one or more wireless communication protocols previously described, e.g. ZigBee®, Bluetooth®, wireless protocols according to IEEE 802.11 standards, a 2G, 3G or 4G telecommunication protocol, ISM band at 433 MHz, WMTS band at 608 MHz and/or the T108 band at 920 MHz.

When operating in the first communication mode, the communications module 23 transmits only the first signal to the medical device. Thus, the first communication mode is effectively a "low-bandwidth" transmission mode in that only the signal having a lower bandwidth is transmitted to the medical device.

When operating in the second communication mode, the communications module transmits at least the second signal to the medical device. Thus, the second communication mode is effectively a "high-bandwidth" transmission mode in that a signal having a higher bandwidth is transmitted to the medical device.

In some embodiments, when operating in the second communication mode, the communications module transmits both the first signal and the second signal to the medical device. This maximizes an amount of information available to the medical device.

In this way, the communications module 23 of the patch sensor 20 is able to adjust the total bandwidth of the signal(s) that is/are transmitted to the medical device without needing to be moved from its position on the subject. This allows control over the amount of power and/or bandwidth (i.e. resources) required by the patch sensor.

A communication path between a patch sensor and a medical device may vary in its available bandwidth (e.g. depending upon which communication channels are available, e.g. number of wireless channels or availability of a wired connection). The proposed invention enables the patch sensor to adjust the bandwidth that is occupies when communicating with the medical device, e.g. to take account of this varying bandwidth of the communication path without needing to move position relative to the subject).

In other words, the patch sensor may be adapted to operate with different bandwidth demands without needing to be moved from its position on the subject.

Moreover, as communicating using a higher bandwidth requires more power and/or processing complexity than communicating using a relatively lower bandwidth, the patch sensor can also be adapted to operate with different power/processing demands without needing to be moved from its position on the subject.

As illustrated, the processing system 22 may comprise a number of other modules that could be shared between the two processing pathways. For example, the processing system may comprise a transducer array front end 24, for controlling an operation of the transducer array, and/or a transducer beam forming module 25, for controlling a pattern of ultrasound emitted by the transducer element.

Thus, the processing system 22 may also be adapted to control an operation of the transducer array 21. The first and second processing pathways may co-operate so as to appropriately control an operation of the transducer array to allow both the first and second signals to be generated by the first and second processing pathways.

The first type of medical data may comprise, for example, physiological data such as vital sign information. Thus, the first processing pathway may process the received echo signal to generate a first signal carrying physiological data. Physiological data (e.g. measured heartrate or blood pressure) can be carried by signals occupying only a low bandwidth, e.g. a low data transmission rate. The physiological data may comprise, for example, raw information which can be used to identify a physiological parameter (such as heart rate) of the subject.

Methods of generating physiological data based on a received echo signal will be readily apparent to the skilled person. For example, a received echo signal may be processed to identify a heart rate or heartbeat of a subject. In particular, the transducer array may include a transducer element that can be operated as a Doppler ultrasound sensor for sensing a Doppler ultrasound signal indicative of the heart activity (e.g. of an unborn child). The Doppler ultrasound sensor may be repurposed to also act as a sensor for ultrasound imaging (e.g. for obtaining a second type of medical data described below) or to detect blood flow rate.

The second type of medical data may comprise, for example, ultrasound imaging data. Ultrasound imaging data may form data suitable for constructing or reconstructing an ultrasound image/video, which construction may be performed by the medical device. Suitable ultrasound transducers and control schemes for obtaining ultrasound imaging data will be readily apparent to the skilled person.

It will be appreciated that these are only possible, albeit preferred, examples of types of first and second data.

In another example, the first type of medical data comprises ultrasound image data for an ultrasound image/video of a first resolution, and the second data comprises ultrasound image data for an ultrasound image/video of a second, greater resolution (which would cause the second signal to require a larger bandwidth than the first signal).

In another example, the first type of medical data comprises ultrasound image data captured at a first frequency and the second data comprises ultrasound image data captured at a second, higher frequency. In such an embodiment, the first processing pathway may comprise a decimating element that removes some of the data from the second signal (e.g. corresponding to certain frames of an ultrasound imaging stream) to thereby generate the first signal occupying less bandwidth.

In yet another example, the first type of medical data comprises first physiological data (e.g. fetal heartrate measured at a first frequency) and the second data comprises physiological data (e.g. fetal heartrate measured at a second, higher frequency). In such an embodiment, the first processing pathway may comprise a decimating element that removes some of the data from the second signal (e.g. corresponding to certain frames of an ultrasound imaging stream) to thereby generate the first signal occupying less bandwidth.

In yet another example, the first type of medical data comprises a first set of physiological data and the second data comprises a second set of physiological data, the second set being greater than the first set (e.g. carrying more physiological information).

Generally speaking, the second signal carries more (medical) data or more complex (medical) data per second than the first signal. Thus, the bandwidth required to transport the second signal is greater than the bandwidth required to transport the first signal.

Preferably, when operating in the second communication mode, the second signal is sent to the medical device with minimal delay, e.g. effectively "real-time" transmission. This requirement is not necessary when operating in the first communication mode, and the first signal and/or first data can be considered as being "low-priority" information. This provides increased flexibility over the use of the patch sensor.

The first and/or second processing pathways may be selectively activated and deactivated. An activated pathway is functional, so that it generates its associated signal. A deactivated pathway is nonfunctional, so that it does not generate its associated signal. This may be achieved through appropriate (de) activation of elements unique to each processing pathway, e.g. by disconnecting a power supply to said element or placing an element in a standby mode, such as the first and/or second processing element 22A, 22B. It will be understood that elements that are shared between different pathways are not deactivated if a particular pathway is deactivated.

The second processing pathway, which generates the second signal, may be deactivated in response to the communications module 23 operating in the first communication mode. Alternatively, the communications module 23 may be controlled to operate in the first communication mode in response to the second processing pathway being deactivated. Thus, there may be an interdependence between the activation of the second processing pathway and the first communication mode of the communications module.

Similarly, depending upon the embodiment, the first processing pathway, which generates the first signal, may be deactivated in response to the communications module 23 operating in the second communication mode. Alternatively, the communications module 23 may be controlled to operate in the second communication mode in response to the first processing pathway being deactivated. Thus, there may be an interdependence between the activation of the first processing pathway and the second communication mode of the communications module. It will be appreciated that this feature cannot be implemented in embodiments in which, when operating in the second communication mode, the communications module 23 transmits both the first and the second signal.

In some embodiments, shared components of the processing system 22 may be modified depending upon the communication mode. For example, the transducer array front end 24 may differ in its control of the operation of the transducer element depending upon the communication mode. Thus, the received echo signal may vary depending upon the communication mode used by the patch sensor.

By way of example, fewer transducers of the transducer array may be used if the communications module is operating in the first communication mode, e.g. if the first signal can be generated based on fewer transducers than the second signal. This may be the case, for example, if the first type of medical data comprises physiological data, such as vital sign information, which may be generated based on the response of only one or two transducers, whereas the second type of medical data may comprise ultrasound imaging data which may require more than two transducers (e.g. if the ultrasound imaging data is for a 3D ultrasound image/video). Other reasons and embodiments would be apparent to the skilled person.

A communication mode controller 26 may be adapted to control a communication mode of the communications module 23. Thus, the communication mode control may select whether the patch sensor uses the first or second communication mode.

In one embodiment, the communication mode controller 26 responds to a user input so as to control the communication mode of the communications module 23. Thus, a user may be able to select whether a first or second signal is transmitted to the medical device by the communications module. The patch sensor 20 may therefore comprise a user interface (not shown) to enable a user to control the communication mode of the communications module.

However, in preferred embodiments, the communication mode controller 26 is (also) adapted to automatically select the communication mode of the communications module 23.

In one example, the communication mode controller responds to an activation or deactivation of a processing pathway to select the communication mode of the communications module. For example, if the second processing pathway (including the second processing element 22B) is deactivated, then the communication mode controller may control the communications module to enter the first communication mode. Selection of the processing pathway may be performed, for example, in response to a user input.

In another example, the communication mode controller responds to an indicated type of the medical device with which the communications module 23 can communicate. In one example, where the first type of medical data comprises physiological data and the second type of medical data comprises ultrasound image data, the communications mode controller is adapted to place the communications module in the second mode if the medical device is a type that can construct or display an ultrasound image (e.g. an ultrasound monitoring device) and in the first mode otherwise, or if the medical device is a physiological parameter monitoring device, e.g. a heart rate monitor.

In preferred examples, the selection of whether a patch sensor uses the first or second communication mode depends upon information about one or more resources available to the patch sensor.

In preferred embodiments, the selection of whether a patch sensor uses the first or second communication mode depends upon characteristics of the communication path between the patch sensor and the medical device. In particular, the selection may be based upon information about a bandwidth available to the patch sensor, i.e. an available bandwidth of the communication path.

For instance, the communication mode controller 26 may be adapted to determine whether there is sufficient bandwidth within the communication path to enable the second signal to be transmitted to the medical device. In response to there being sufficient bandwidth, the communication mode controller may control the communications module to enter the second communication mode.

In one realization of such an embodiment, the communication mode controller may be adapted to determine if there is a wired connection between the communications module and the medical device. In response to their being a wired connection, the communication mode controller can conclude that there is sufficient bandwidth to facilitate the transport of the second signal and control the communications module to operate in the second communication mode.

In another realization, the communication mode controller may be adapted to determine whether a wireless connection between the communications module and the medical device is able to facilitate the transport of the second signal to the medical device (e.g. with a suitable level of reliability).

An example of a method of identifying which communication mode a controller should use, based upon bandwidth availability, will be described later.

The patch sensor 20 comprises a power source 29, such as a battery or cell. The power source 29 provides power for powering the other components of the patch sensor, e.g. via one or more power lines (not shown). In some examples, the power source comprises a connection to a main supply (or other power supply, such as one provided by the medical device). This connection to the mains supply may be provided by one or more wires connected to the communications module, e.g. via a USB (or other wired communication protocol) connection that also provide a wired communication channel between the communications module and a medical device. Thus, the power source 29 may draw from a mains supply.

In such embodiments, the communication mode controller may select whether the patch sensor uses the first or second communication mode based upon information about a type or power level of the power source available for use by the patch sensor.

By way of example only, the communications mode controller may place the communications module in the first communication mode if the power source comprises only a battery or cell. The communications mode controller may place the communications module in the second communication mode if the power source draws power from a mains supply.

As another example, the communications mode controller may place the communications module in the first communication mode if the power source has less than or equal to a predetermined power level of the power source. The predetermined power level may be any value between 10% and 60% of the maximum power level of the power source. Similarly, the communications mode controller may place the communications module in the second communication mode if the power source has more than the predetermined power level of the power source. Thus, when less power is available, the communication mode of the communications module may switch to a lower consumption operational mode.

In some embodiments, the communications mode controller sets the communication mode of the communications module based on a combination of bandwidth availability and information about a type or power level of the power source for the patch sensor. For example, may place the communications module in the second communication mode only if the power source draws power from a mains supply and there is sufficient bandwidth to transmit the second signal to the medical device. Other suitable combinations will be readily apparent to the skilled person, e.g. placing the communications module in the first communication mode if a remaining power level of a power source falls below a predetermined value or there is insufficient bandwidth to transmit the second signal.

Figure 3:
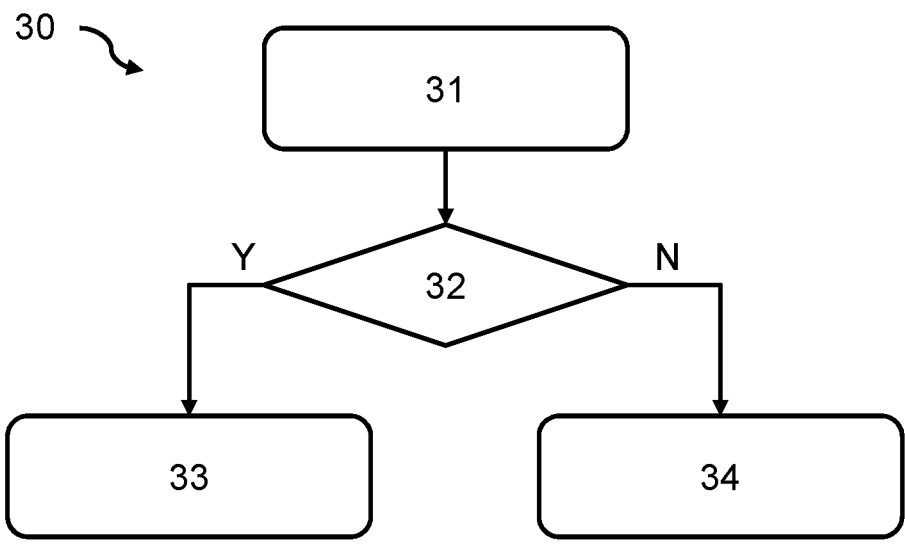
FIG. 3 illustrates a method according to an embodiment.

FIG. 3 illustrates a method 30 of identifying which communication mode a controller should use according to an embodiment of the invention. Such an operation may be performed by the communication mode controller.

The method 30 effectively determines a bandwidth available to the patch sensor, and selects the communication mode based on the available bandwidth.

The method 30 comprises a step 31 of identifying one or more available communication channels over which the communications module is able to communicate with the medical device.

Thus, step 31 may comprise identify how, and over which channels, the communications module is able to communicate with the medical device. This may comprise identifying available wireless channels for communication with the medical device and/or whether a wired channel is available for communication with the medical device.

In embodiments, a wireless channel may be considered "available" if is it unoccupied by another device in the near vicinity, e.g. if a noise level of that wireless channel is below a predetermined value or if a received signal strength indicator of a wireless channel is above a predetermined threshold (i.e. a channel is "available"). Other methods of identifying whether a wireless channel is available for communication will be apparent to the skilled person, e.g. by identifying a wireless communication protocol used by the communications module and identifying available wireless channels associated with that protocol.

Methods or processes for identifying whether there is a wired channel to the medical device would be apparent to the skilled person. In one embodiment, the communications module or communication mode controller may receive a signal from a medical device connected to a wired terminal of the communications module, indicating that there is a wired channel between the communications module and the medical device. In another embodiment, an impedance at the wired terminal may be monitored, with a reduction in impedance indicating that a wire connects the wired terminal to the medical device.

The method 30 further comprises a step 32 of determining whether or not any of the identified communication channels have sufficient bandwidth to facilitate the transport of the second signal to the medical device.

In a simple embodiment, step 32 may comprise determining that there is sufficient bandwidth to facilitate the transport of the second signal if a wired channel is available (e.g. and not otherwise). This is because a wired channel will generally have sufficiently high bandwidth to transport high-bandwidth signals. Thus, steps 31 and 32 may, in some embodiments, be combined into a single step of determining whether or not a wired channel is available for communicating with the medical device.

In some embodiments, step 32 may comprise determining whether any of the wireless channels have sufficient bandwidth (e.g. in Kbps) to facilitate the transport of the second signal. This may comprise comparing the bandwidth required by the second signal to an available bandwidth of each identified wireless channel. The bandwidth required by the second signal will vary in different embodiments, e.g. based on the particular implementation of the second type of medical data carried by the second signal.

Thus, in embodiments, step 32 may comprise determining whether any of the wireless channels has a bandwidth above or equal to a pre determined bandwidth. The predetermined bandwidth may be a value equal to or greater than a bandwidth required to transport the second signal. In some embodiments, the predetermined bandwidth is no less than 100 kbits/s, for example, no less than 500 kbits/s, for example, no less than 1 Mbit/s.

A wireless channel may, if already occupied by another device, have a reduced available bandwidth compared to its maximum available bandwidth, e.g. if the channel uses a time-division multiplexing system. Step 32 may therefore comprise a sub-step of monitoring each identified available wireless channel to determine an available bandwidth.

The method 30 further comprises a step 33 of placing the communications module in the second communication mode in response to determining that at least one of the identified communications channels has sufficient bandwidth to transmit the second signal to the medical device.

The method 30 further comprises a step 34 of placing the communications module in the first communication mode in response to determining that none of the identified communications channels has sufficient bandwidth to transmit the second signal to the medical device.

Thus, the communications module may be controlled so as to transmit the second signal to the medical device in response to a communication path (available to the communications module) between the communications module and the medical device having sufficient available bandwidth to carry the second signal.

If a wired channel is available, the second communication mode preferably comprises communicating when operating in the second communication mode, transmitting (at least) the second signal to the medical device over the wired channel.

If a wired channel is not available, but at least one wireless channel has sufficient bandwidth to facilitate the transport of the second signal, the second communication mode may comprise transmitting at least the second signal to the medical device over the at least one wireless channel.

In some embodiments, the patch sensor is adapted to use different communication channels (and/or a different number of channels) when operating in the first and second communication modes. For example, when operating in the second communication mode, a wired channel may be used, whereas, when operating in the first communication mode, a wireless channel may be used. As another example, when operating in the first communication mode, a first wireless channel (according to a first communication protocol) may be used, and when operating in the second communication mode, a second wireless channel (e.g. according to a second, different communication protocol) may be used.

The above-described patch sensors are suitable for use with different medical devices. In particular, when the communications module is operating in the second communication mode, the patch sensor may be suitable for communication with an ultrasound monitoring device, e.g. comprising an ultrasound image display. When the communications module is operating in the first control mode, the patch sensor may be suitable for communication with a physiological monitoring device (e.g. a heart-rate monitor).

Thus, the patch sensor may act as a different type of sensor for different types of patient monitoring systems without needing to move position on the patient or subject.

Each element of the described patch sensor may be appropriately adapted to act as an appropriate step of a method for transmitting one or more signals to a medical device.

Thus, there is proposed a method of transmitting one or more signals to a medical device. The method comprises steps of transmitting ultrasound waves and receiving echo information to thereby generate a received echo signal. The method also comprises a step of processing the received echo signal, using a first processing pathway of a processing system, to generate a first signal carrying a first type of medical data derived from the received echo signal. The method also comprises a step of processing the received echo signal, using a second processing pathway of the processing system, to generate a second signal carrying second, different data derived from the received echo signal, the second signal occupying a greater bandwidth than the first signal. The method also comprises operating a communications module, adapted to transmit one or more signals to the medical device, in either: a first communication mode, in which the communications module transmits only the first signal to the medical device; and a second communication mode, in which the communications module transmits at least the second signal to the medical device.

The skilled person would appreciate that whilst only first and second types of medical data (i.e. first and second data), signals and communication modes are envisaged, other embodiments may employ more than two such features.

For example, the processing system may comprise N processing pathways (where N is at least two), each adapted to generate a respective Nth signal, carrying Nth data, each of the N signals occupying a different bandwidth. The communications module may be operable in N different communication modes, in which (at least or only) the Nth signal is transmitted to the medical device.

Moreover, the communications module may be operable in a third communication mode, in which only the second signal is transmitted to the medical device. A communication mode controller may place the communications module in the third communication mode based on information about available resources of the patch sensor. For example, the communication mode controller may place the communications module in the third communication mode if there is sufficient bandwidth to transmit the second signal, but insufficient bandwidth to transmit both the first and second signal, to the medical device.

In another example, a communication mode controller may place the communications module in the third communication mode if a remaining power level of a power source falls between a first and second predetermined power level (e.g. between 20 and 60%). In such an embodiment, the communications module may be placed in the second communication mode, in which both the first and second signals are sent to the medical device, if the remaining power level is above the second predetermined power level and be placed in the first communication mode, in which only the first signal is sent to the medical device, if the remaining power level is below the first predetermined power level.

In some embodiments, the communications module may be operable in a non-communicative mode, in which no signals are transmitted to the medical device. The communication mode controller may place the communications module in the non-communicative mode, for example, if there is insufficient bandwidth to transmit the first signal.

The skilled person would be readily capable of adapting a sensor and/or processing system and/or the communication mode controller for carrying out any herein described method. Thus, each step of the flow chart may represent a different action performed by a communication mode controller, and may be performed by a respective module of the communication mode controller.

Embodiments may therefore make use of a processing system. The processing system and/or communication mode controller can be implemented in numerous ways, with software and/or hardware, to perform the various functions required. A processor is one example of a processing system which employs one or more microprocessors that may be programmed using software (e.g., embedded firmware) to perform the required functions. A processing system and/or communication mode controller may however be implemented with or without employing a processor, and also may be implemented as a combination of dedicated hardware to perform some functions and a processor (e.g., one or more programmed microprocessors and associated circuitry) to perform other functions.

Examples of processing system and/or communication mode controller components that may be employed in various embodiments of the present disclosure include, but are not limited to, conventional microprocessors, application specific integrated circuits (ASICs), and field-programmable gate arrays (FPGAs).

In various implementations, a processor and/or processing system and/or communication mode controller may be associated with one or more storage media such as volatile and non-volatile computer memory such as RAM, Flash, PROM, EPROM, and EEPROM. The storage media may be encoded with one or more programs that, when executed on one or more processors and/or processing systems, perform the required functions. Various storage media may be fixed within a processor or processing system or may be transportable, such that the one or more programs stored thereon can be loaded into a processor or processing system.

It will be understood that disclosed methods are preferably computer-implemented methods. As such, there is also proposed the concept of computer program comprising code means for implementing any described method when said program is run on a processing system, such as a computer. Thus, different portions, lines or blocks of code of a computer program according to an embodiment may be executed by a processing system or computer to perform any herein described method. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

Figure 4:
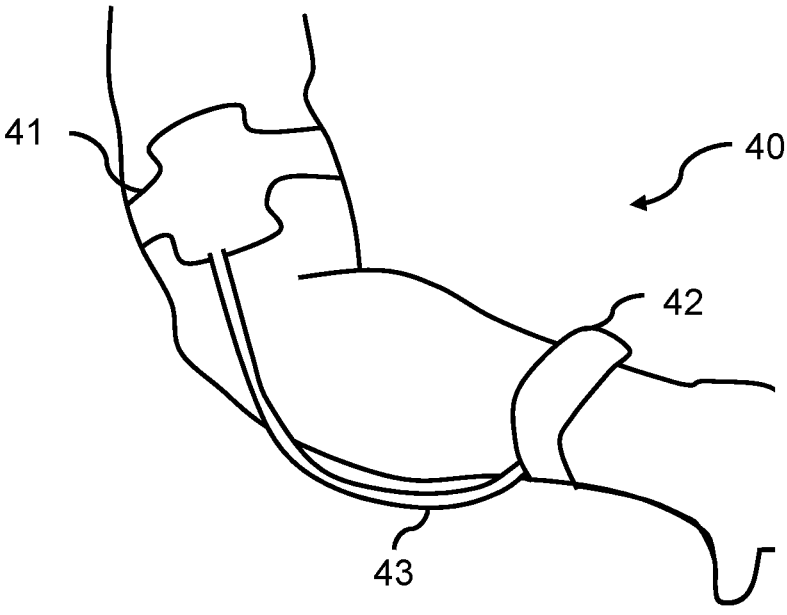
FIG. 4 illustrates an embodiment of a patch sensor.

FIG. 4 illustrates a patch sensor 40 according to an embodiment of the invention. The patch sensor 40 is mountable of a part of the subject, here the arm, using one or more straps. The patch sensor 40 comprises a transducer array 41. The patch sensor also comprises a processing system and communications module, here formed in a single unit 42. The transducer array 41 and single unit 42 are connected by a wire 43. The various components of the patch sensor 40 may be formed according to any previously described embodiment.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A patch sensor adapted to transmit one or more signals to a medical device, the patch sensor comprising:
  a transducer array adapted to transmit ultrasound waves and receive echo information to thereby generate a received echo signal;
  a processing system defining:
    a first processing pathway adapted to process the received echo signal to generate a first signal carrying physiological data derived from the received echo signal; and
    a second processing pathway adapted to process the received echo signal to generate a second signal carrying ultrasound imaging data derived from the received echo signal, the second signal occupying a greater bandwidth than the first signal; and
  a communications module adapted to transmit one or more of the first and second signals to the medical device, the communications module being operable in:
    a first communication mode, in which the communications module transmits the first signal over a first communication channel, and does not transmit the second signal, to the medical device; and a second communication mode, in which the communications module transmits at least the second signal over a second communication channel to the medical device, wherein the second communication channel has a greater bandwidth than the first communication channel.

2. The patch sensor of claim 1, wherein the communication module is adapted to:
  when operating in the first communication mode, transmit the first signal to a physiological data monitor which thereby acts as the medical device; and
  when operating in the second communication mode, transmit at least the second signal to an ultrasound monitoring system which thereby acts as the medical device.

3. The patch sensor of claim 1, wherein the first communication channel comprises a wireless channel and the communications module comprises a wireless transmitter, and wherein the communications module is adapted to, when operating in the first communication mode, wirelessly transmit the first signal to the medical device using the wireless transmitter.

4. The patch sensor of claim 1, wherein the second communication channel comprises a wired channel and the communications module comprises a wired terminal, for connecting to a wire connected to the medical device, and wherein the communications module is adapted to, when operating in the second communication mode and when a wire is connected to the wired terminal, transmit at least the second signal to the medical device over the wire connected to the wired terminal.

5. The patch sensor of claim 1, further comprising a communication mode controller adapted to control the communications module to enter the first or second communication mode based on information about one or more resources available to the patch sensor.

6. The patch sensor of claim 5, wherein the information about one or more resources comprises information about: a type of power source used by the patch sensor; a type of the medical device; a power level of a power source used by the patch sensor; and an available bandwidth for communicating with the medical device.

7. The patch sensor of claim 5, wherein the communication mode controller is adapted to:
  identify one or more available communication channels over which the communications module is able to communicate with the medical device;
  determine whether or not any of the identified communication channels have sufficient bandwidth to facilitate transport of the second signal to the medical device as the second communication channel;
  place the communications module in the second communication mode in response to determining that at least one of the identified communication channels has sufficient bandwidth to transmit the second signal to the medical device; and
  place the communications module in the first communication mode in response to determining that none of the identified communication channels has sufficient bandwidth to transmit the second signal to the medical device.

8. The patch sensor of claim 7, wherein:
  the communications module comprises a wired terminal, for transmitting one or more signals via a wire connected thereto; and
  the communication mode controller is adapted to:

determine whether a wire is connected between the wired terminal and the medical device to thereby identify whether a wired communication channel to the medical device is available as the second communication channel; and place the communications module in the second communication mode in response to determining that the wired communication channel is available.

9. The patch sensor of claim 5, wherein:

the communications module comprises a wireless transmitter for transmitting signals to the medical device; and the communication mode controller is adapted to:

identify one or more available wireless communication channels over which the wireless transmitter is able to transmit a signal to the medical device;

determine an available bandwidth of each available wireless communication channel;

determine whether or not any of the identified available wireless communication channels have sufficient available bandwidth to facilitate transport of the second signal to the medical device as the second communication channel; and place the communications module in the second communication mode in response to determining that at least one available wireless communication channel has sufficient bandwidth to facilitate the transport of the second signal to the medical device.

10. The patch sensor of claim 5, wherein the communication mode controller is further adapted to control the communications module to automatically switch from the first communication mode to the second communication mode when the second communication mode becomes available.

11. The patch sensor of claim 1, wherein the communications module is adapted to, when operating in the second communication mode, transmit both the first signal and the second signal over the second communication channel to the medical device.

12. The patch sensor of claim 1, further comprising a subject securing mechanism adapted to secure the patch sensor to a position on a subject, wherein the communications module is adapted to be switchable between the first and second communication mode whilst the patch sensor remains in the same position on the subject.

13. A monitoring system comprising:

the patch sensor according to claim 1; and the medical device adapted to receive the one or more signals from the patch sensor.

14. The patch sensor of claim 1, wherein the communications module is operable in the first communication mode to reduce a power consumption of the patch sensor.

15. The patch sensor of claim 1, wherein the communications module is further adapted to deactivate the second processing pathway when the communications module is in the first communication mode, and to deactivate the first processing pathway when the communications module is in the second communication mode.

16. A method of controlling a patch sensor wearable by a subject and comprising a transducer array for transmitting ultrasound waves into the subject, a processing system for receiving and processing an echo signal responsive to the transmitted ultrasound waves, and a communications module for communicating with a medical device, the method comprising:

generating a first signal carrying physiological data derived from the received echo signal in a first processing pathway;

generating a second signal carrying ultrasound imaging data derived from the received echo signal in a second processing pathway, the second signal occupying a greater bandwidth than the first signal;

identifying one or more available communication channels over which the communications module is able to communicate with the medical device;

determining whether or not any of the identified communication channels have sufficient bandwidth to facilitate transport of the second signal to the medical device;

placing the communications module in a second communication mode in response to determining that at least one of the identified communication channels has sufficient bandwidth to transmit the second signal to the medical device, and transmitting at least the second signal over the at least one of the identified communication channels to the medical device in the second communication mode; and placing the communications module in a first communication mode in response to determining that none of the identified communication channels has sufficient bandwidth to transmit the second signal to the medical device, and transmitting the first signal over another one of the identified communication channels to the medical device in the first communication mode, and not transmitting the second signal, wherein the another one of the identified communication channels has insufficient bandwidth to transmit the second signal.

17. The method of claim 16, further comprising:

determining a type of power source powering the patch sensor;

when the type of power source is resource-restricted, placing the communications module in the first communication mode; and when the type of power source is not resource-restricted, placing the communications module in the second communication mode.

18. The method of claim 16, further comprising:

deactivating the second processing pathway when the communications module is in the first communication mode; and deactivating the first processing pathway when the communications module is in the second communication mode.

19. The method of claim 16, wherein:

when in the first communication mode, the first signal is transmitted to a physiological data monitor which thereby acts as the medical device, and when in the second communication mode, at least the second signal is transmitted to an ultrasound monitoring system which thereby acts as the medical device.

20. A non-transitory computer readable medium storing code for controlling a patch sensor wearable by a subject and comprising a transducer array for transmitting ultrasound waves into the subject, a processing system receiving and processing an echo signal responsive to the transmitted ultrasound waves, and a communications module for communicating with a medical device, wherein when executed by one or more processors, the code causes the one or more processors to:

generate a first signal carrying physiological data derived from the received echo signal in a first processing pathway;

generate a second signal carrying ultrasound imaging data derived from the received echo signal in a second processing pathway, the second signal occupying a greater bandwidth than the first signal;

identify one or more available communication channels over which the communications module is able to communicate with the medical device;

determine when any of the identified communication channels have sufficient bandwidth to facilitate transport of the second signal to the medical device;

place the communications module in a second communication mode in response to determining that at least one of the identified communication channels has sufficient bandwidth to transmit the second signal to the medical device, and causing at least the second signal to be transmitted over the at least one of the identified communication channels to the medical device in the second communication mode; and placing the communications module in a first communication mode in response to determining that none of the identified communication channels has sufficient bandwidth to transmit the second signal to the medical device, and causing the first signal to be transmitted over another one of the identified communication channels to the medical device, and not transmitting the second signal, in the first communication mode, wherein the another one of the identified communication channels has insufficient bandwidth to transmit the second signal.

\* \* \* \* \*